(12) United States Patent
Matsuura et al.

(10) Patent No.: US 11,324,435 B2
(45) Date of Patent: May 10, 2022

(54) HEARTBEAT DETECTION METHOD AND HEARTBEAT DETECTION DEVICE

(71) Applicant: NIPPON TELEGRAPH AND TELEPHONE CORPORATION, Tokyo (JP)

(72) Inventors: Nobuaki Matsuura, Tokyo (JP); Kei Kuwabara, Tokyo (JP); Takayuki Ogasawara, Tokyo (JP); Ryoichi Kasahara, Tokyo (JP); Koji Fujii, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 162 days.

(21) Appl. No.: 16/342,174

(22) PCT Filed: Sep. 25, 2017

(86) PCT No.: PCT/JP2017/034444
§ 371 (c)(1),
(2) Date: Apr. 15, 2019

(87) PCT Pub. No.: WO2018/074145
PCT Pub. Date: Apr. 26, 2018

(65) Prior Publication Data
US 2019/0320926 A1    Oct. 24, 2019

(30) Foreign Application Priority Data
Oct. 17, 2016   (JP) .............................. JP2016-203352

(51) Int. Cl.
*A61B 5/0456*  (2006.01)
*A61B 5/00*  (2006.01)
(Continued)

(52) U.S. Cl.
CPC ............ *A61B 5/352* (2021.01); *A61B 5/7203* (2013.01); *G16H 40/63* (2018.01)

(58) Field of Classification Search
CPC ... A61B 5/0245; A61B 5/0456; A61B 5/7203; G16H 40/63
(Continued)

(56) References Cited

U.S. PATENT DOCUMENTS

| 5,092,340 A | 3/1992 | Yamaguchi et al. |
| 5,564,430 A | 10/1996 | Jacobson et al. |

(Continued)

FOREIGN PATENT DOCUMENTS

| CN | 103300848 A | 9/2013 |
| CN | 106687033 A | 5/2017 |

(Continued)

OTHER PUBLICATIONS

Chung, Peter, "ECG Implementation on the TMS320C5515 DSP Medical Development Kit (MDK) with the ADS1298 ECG-HE", Texas Instruments Incorporated, Application Report SPRABJ1, Jan. 2011, 20 pages.

(Continued)

*Primary Examiner* — Carl H Layno
*Assistant Examiner* — Jane C Kalinock
(74) *Attorney, Agent, or Firm* — Womble Bond Dickinson (US) LLP

(57) ABSTRACT

A heartbeat detection device including a time difference value calculation unit to calculate a time difference value from a sampling data string of an electrocardiographic waveform of a living body, an index value calculation unit to calculate an index value for heartbeat detection based on the time difference value, a threshold setting unit to determine whether a peak of the index value exceeding a threshold can be detected, to calculate, a threshold candidate based (Continued)

on an average value of the predetermined number of the most recent peaks among these peaks. A threshold candidate is set as a new threshold when the threshold candidate has a value equal to or less than a threshold limit value. A heartbeat time determination unit sets the sampling time of the peak as the heartbeat time when the peak of the index value exceeding the threshold is detected.

6 Claims, 17 Drawing Sheets

(51) Int. Cl.
*A61B 5/352* (2021.01)
*G16H 40/63* (2018.01)

(58) Field of Classification Search
USPC .......................................... 600/509, 519, 521
See application file for complete search history.

(56) References Cited

U.S. PATENT DOCUMENTS

| | | | |
|---|---|---|---|
| 2012/0238892 A1* | 9/2012 | Sarkar .................. | A61N 1/3621 600/516 |
| 2013/0237868 A1 | 9/2013 | Choi et al. | |
| 2014/0073975 A1* | 3/2014 | Engelbrecht ......... | A61B 5/7203 600/502 |
| 2017/0281021 A1* | 10/2017 | Matsuura ............. | A61B 5/0456 |

FOREIGN PATENT DOCUMENTS

| | | |
|---|---|---|
| JP | 07-067844 A | 3/1995 |
| JP | 2013-184062 A | 9/2013 |
| KR | 10-2013-0103259 A | 9/2013 |
| WO | 2016/035701 A1 | 3/2016 |
| WO | 2016/039182 A1 | 3/2016 |
| WO | 2017/150156 A1 | 9/2017 |

OTHER PUBLICATIONS

International Preliminary Reporton Patentability received for PCT Patent Application No. PCT/JP2017/034444, dated May 2, 2019, 12 pages (7 pages of English Translation and 5 pages of Original Document).

International Search Report and Written Opinion received for PCT Patent Application No. PCT/JP2017/034444, dated Nov. 7, 2017, 14 pages (7 pages of English Translation and 7 pages of Original Document).

Yamasawa, "Easy-to-Understand Electrocardiogram, Reveal Heart Disease from 12-lead Electrocardiogram", Elsevier Japan, 2003, 6 pages (2 page of English Translation Cover Sheet and 4 pages of original document).

Supplementary European Search Report and Search Opinion received for EP Patent Application No. 17862105.8, dated Feb. 19, 2020, 8 pages.

* cited by examiner

HEARTBEAT DETECTION METHOD AND HEARTBEAT DETECTION DEVICE

TECHNICAL FIELD

The present invention relates to a technology of extracting biological information such as a heartbeat interval (R-R interval) from an electrocardiographic waveform and, more particularly, to a heartbeat detection method and heartbeat detection device for detecting a heartbeat while acquiring an electrocardiographic waveform in real time.

BACKGROUND ART

Measuring a heartbeat by a body-worn device capable of measuring an ECG (Electrocardiogram) waveform is useful as such a measured heartbeat can be used for controlling the load intensity of training in sports, evaluating the autonomic function in daily life, and the like. In recent years, a shirt-type device with electrodes has been developed, and heartbeat monitoring has been performed more easily in various scenes.

As a method of detecting a heartbeat (R wave) from an ECG waveform, a method of detecting a peak in time series is convenient. That is, a threshold is set for the time series of the sampling data of the ECG waveform. When the sampling data exceeds the threshold, an R wave is detected.

When an R wave is detected based on not the ECG waveform itself but a data string obtained by calculating the time difference of the ECG waveform, the following advantages can be achieved: (I) undulation in a baseline is canceled; and (II) a peak can be detected even if an S wave is larger than an R wave due to individual differences and the like. Furthermore, an index is calculated by taking into consideration a clearance formed before and after a peak, and also by noticing the fact that the widths of the peaks derived from a Q wave, an R wave, and an S wave are almost constant and without any individual differences. The R wave can be detected with more accuracy when time series of the calculated indices are used.

When detecting an R wave using a threshold, for example, there is proposed a method of setting the threshold based on the maximum value of a data string for the first 2 seconds, and updating the threshold based on the average value of peak values every five heartbeats (see, for example, Non-Patent Literature 1). In this method, it is possible to reflect the trend of a signal level on the threshold.

However, when acquiring an ECG waveform, noises may be added to the waveform. Especially in wearable devices that are worn by bodies of subjects, a disturbance of an ECG waveform is more likely to occur. In particular, noise with a very large amplitude that cannot be obtained from the cardiac potential of a human may be mixed into the ECG waveform due to floating of an electrode or the like. When such a large noise is added, the threshold may jump due to the effect of the noise, and an R wave may not be detected afterwards.

To solve this problem, Patent Literature 1 discloses an arrangement of optimizing a threshold in consideration of noise in an ECG waveform.

RELATED ART LITERATURE

Patent Literature

Patent Literature 1: Japanese Patent Laid-Open No. 07-067844

Non-Patent Literature

Non-Patent Literature 1: "ECG Implementation on the TMS320C5515 DSP Medical Development Kit (MDK) with the ADS1298 ECG-FE", Texas Instruments Incorporated, 2011

DISCLOSURE OF INVENTION

Problem to be Solved by the Invention

As described above, in the conventional heartbeat detection method, when a large noise is added to an ECG waveform, a threshold may jump due to the effect of the noise, and an R wave may not be detected afterwards. To solve this problem, Patent Literature 1 discloses an arrangement of optimizing a threshold.

However, Patent Literature 1 does not disclose details of detection result information for determining whether a threshold level is an appropriate level or not, and it may thus be difficult to optimize the threshold when the threshold jumps due to the presence of noise in the electrocardiographic waveform.

The present invention has been made in consideration of the above problem, and has as its object to provide a heartbeat detection method and heartbeat detection device capable of appropriately detecting a heartbeat even if a noise is superimposed on an electrocardiographic waveform.

Means of Solution to the Problem

According to the present invention, there is provided a heartbeat detection method including, a first step of calculating, for each sampling time, a time difference value of sampling data from a sampling data string of an electrocardiographic waveform of a living body, a second step of calculating an index value for heartbeat detection based on the time difference value calculated in the first step, a third step of determining whether a peak of the index value exceeding a current threshold is detected, and when consecutively detecting equal to or greater than a predetermined number of peaks, calculating a threshold candidate based on an average value of most recent predetermined number of peaks among the peaks of equal to or greater than the predetermined number that are being detected, a fourth step of comparing the threshold candidate calculated in the third step with a threshold limit value based on a difference limit value that is likely be a time difference value of the electrocardiographic waveform of the living body, not updating the threshold when the threshold candidate exceeds the threshold limit value, and setting the threshold candidate as a new threshold when the threshold candidate has a value that is equal to or less than the threshold limit value, and a fifth step of setting, when detecting a peak of the index value that exceeds the threshold, a sampling time of the peak as a heartbeat time.

According to the present invention, there is also provided a heartbeat detection device including, a time difference value calculation unit configured to calculate, for each sampling time, a time difference value of sampling data from a sampling data string of an electrocardiographic waveform of a living body, an index value calculation unit configured to calculate an index value for a heartbeat detection based on the time difference value calculated by the time difference value calculation unit, a threshold setting unit configured to determine whether a peak of the index value that exceeds a current threshold is detected, configured to calculate, when consecutively detecting equal to or greater than a predetermined number of peaks, a threshold candidate based on an average value of most recent predetermined number of peaks among the peaks of equal to or greater than the predetermined number that are being detected, configured not to update the threshold when the threshold candidate exceeds a threshold limit value based on a difference limit value that is likely be a time difference value of the electrocardiographic waveform of the living body, and configured to set the threshold candidate as a new threshold when the threshold candidate has a value that is equal to or less than the threshold limit value, and a heartbeat time determination unit configured to set the sampling time of the peak as the heartbeat time when the peak of the index value exceeding the threshold is detected.

Effect of the Invention

According to the present invention, a time difference value is calculated from a sampling data string of an electrocardiographic waveform of a living body, an index value for a heartbeat detection is calculated based on the time difference value, a threshold candidate is calculated based on the average value of a predetermined number of most recent peaks among peaks of the index value exceeding a current threshold, and the threshold candidate is compared with a threshold limit value based on a difference limit value that is likely be the time difference value of the electrocardiographic waveform of the living body. Then, when the threshold candidate exceeds the threshold limit value, the threshold is not updated, and when the threshold candidate is equal to or less than the threshold limit value, the threshold candidate is set as a new threshold. Therefore, even if large noise is mixed in the electrocardiographic waveform, it is possible to prevent the threshold used for heartbeat detection from jumping off. As a result, according to the present invention, it is possible to detect a heartbeat more appropriately even if noise is superimposed on the electrocardiographic waveform.

BEST MODE FOR CARRYING OUT THE INVENTION

First Embodiment

Figure 1:
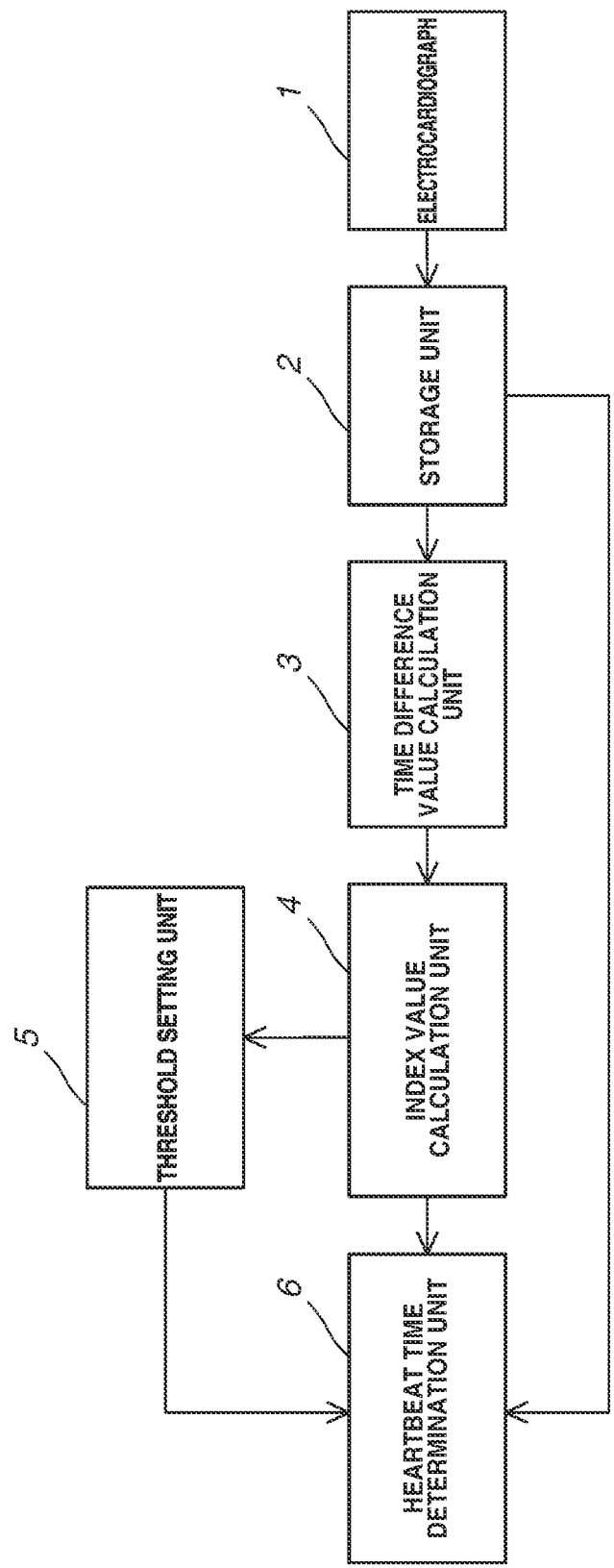
FIG. 1 is a block diagram showing the arrangement of a heartbeat detection device according to the first embodiment of the present invention.
Figure 2:
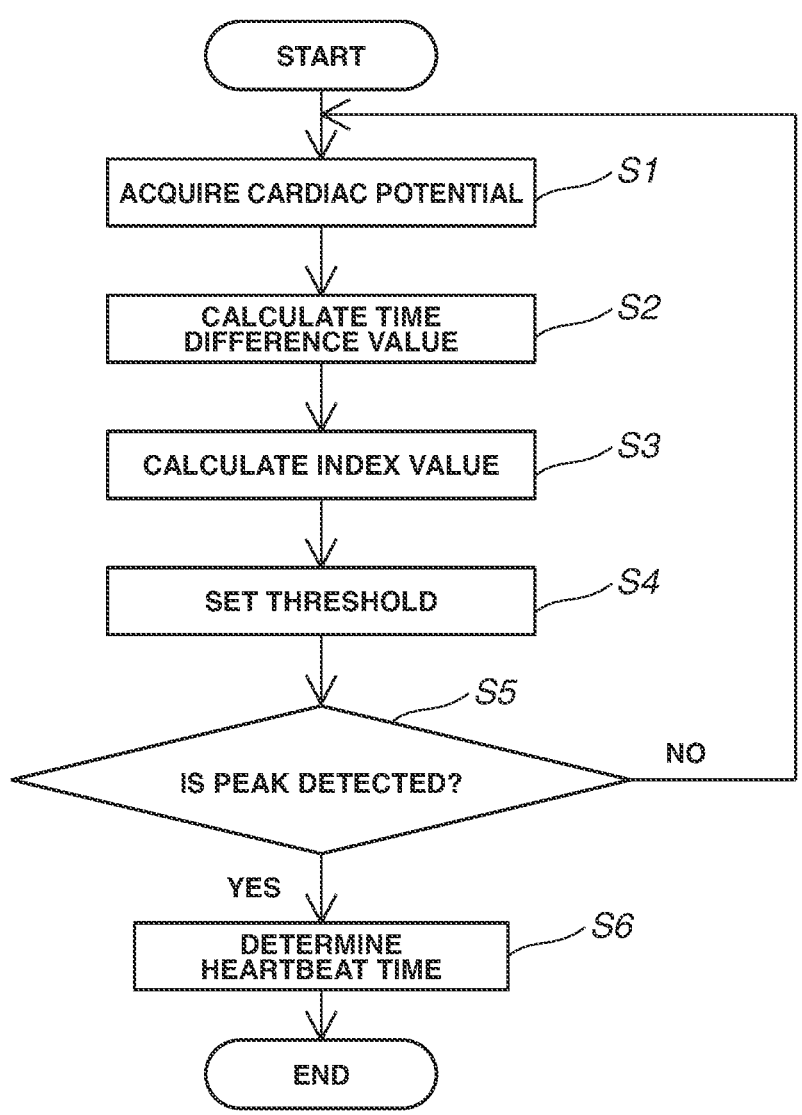
FIG. 2 is a flowchart for explaining a heartbeat detection method according to the first embodiment of the present invention.

The embodiment of the present invention will be described below with reference to the accompanying drawings. FIG. 1 is a block diagram showing the arrangement of a heartbeat detection device according to the first embodiment of the present invention. FIG. 2 is a flowchart for explaining a heartbeat detection method according to the first embodiment of the present invention. The heartbeat detection device includes an electrocardiograph 1 that outputs the sampling data string of an ECG waveform, a storage unit 2 that stores sampling data string of the ECG waveform and sampling time information, a time difference value calculation unit 3 that calculates, for each sampling time, the time difference value of sampling data from the sampling data string of the ECG waveform, an index value calculation unit 4 that calculates an index value for heartbeat detection based on the time difference value calculated by the time difference value calculation unit 3, a threshold setting unit 5 that sets a threshold to be compared with the index value, and a heartbeat time determination unit 6 that sets, when a peak of the index value exceeding the threshold is detected, the sampling time of the peak as the heartbeat time.

The heartbeat detection method according to this embodiment will be described below. In this embodiment, x(n) represents a data string obtained by sampling the ECG waveform where n (n=1, 2, . . . ) represents a number assigned to one sampling data. The greater the number n is, the later the sampling time becomes, as a matter of course.

The electrocardiograph 1 measures the ECG waveform of a living body (human body) (not shown), and outputs the sampling data string x(n) of the ECG waveform. At this time, the electrocardiograph 1 outputs the sampling data string by adding sampling time information to each sampling data. Note that a practical method of measuring the ECG waveform is a well-known technique and a detailed description thereof will be omitted.

The storage unit 2 stores the sampling data string x(n) of the ECG waveform and the sampling time information, which have been output from the electrocardiograph 1.

To calculate a time difference value y(n) of the sampling data x(n), the time difference value calculation unit 3 acquires, from the storage unit 2, data x(n+1) one sampling operation after the sampling data x(n) and data x(n−1) one sampling operation before the sampling data x(n) (step S1 of FIG. 2). Then, the time difference value calculation unit 3 calculates the time difference value y(n) of the sampling data x(n) for each sampling time (step S2 of FIG. 2) by:

$$y(n)=x(n+1)-x(n-1) \quad (1)$$

Figure 3:
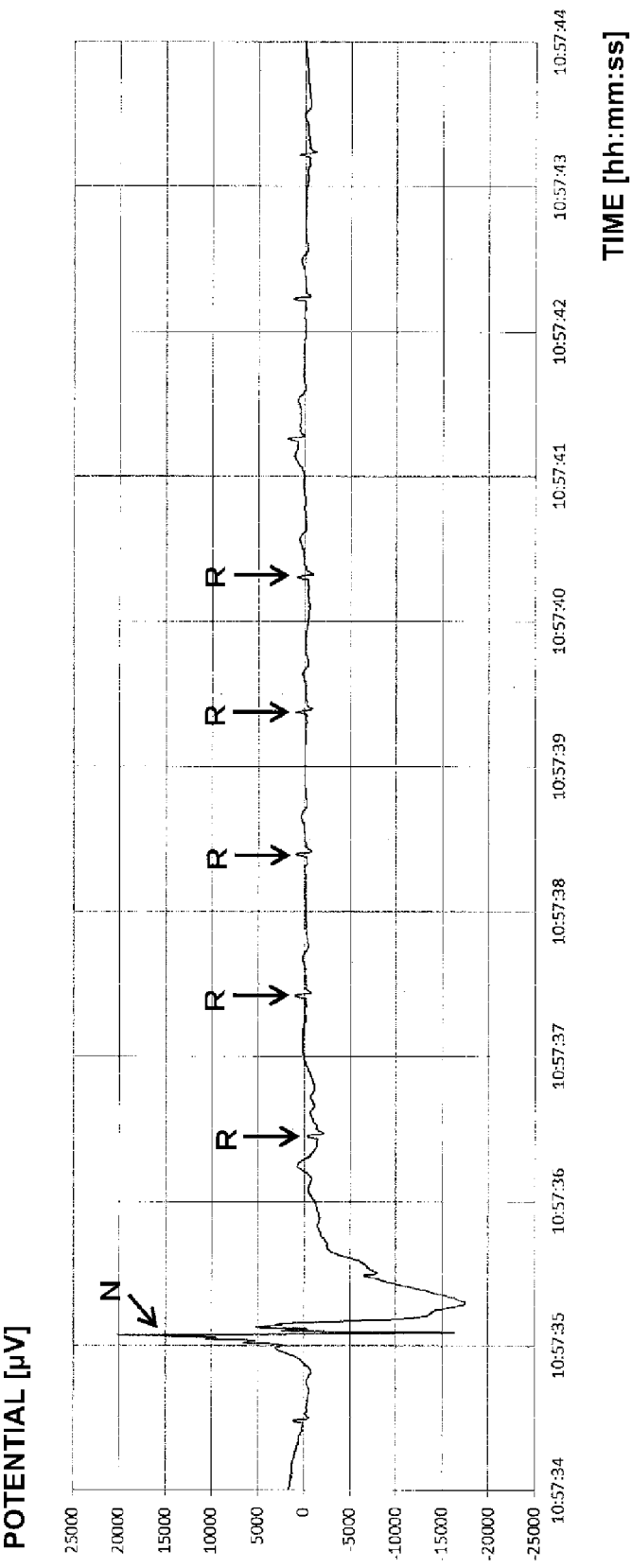
FIG. 3 is a timing chart showing an example of an electrocardiographic waveform.

FIG. 3 is a timing chart showing an example of the ECG waveform. In FIG. 3, "R" represents an R wave to be detected as a heartbeat. Referring to FIG. 3, the abscissa represents time, and the ordinate represents a cardiac potential [μV]. In the example shown in FIG. 3, the waveform is largely disturbed at a position of "N". In the ECG waveform of the human, the amplitudes of Q, R, and S waves depend on a lead but are about 2,500 to 3,000 μV at most. When, for example, the amplitude of the wave exceeds 3.6 mV (36 mm on an electrocardiographic recording paper), the wave is determined to be abnormal (see Yamasawa, "Easy-to-Understand Electrocardiogram, Reveal Heart Disease from 12-lead Electrocardiogram", Elsevier Japan, 2003). The disturbance of the waveform at the position of "N" has an amplitude from +20,000 to −15,000 μV, and is apparently caused not by the cardiac potential but by noise.

Figure 4:
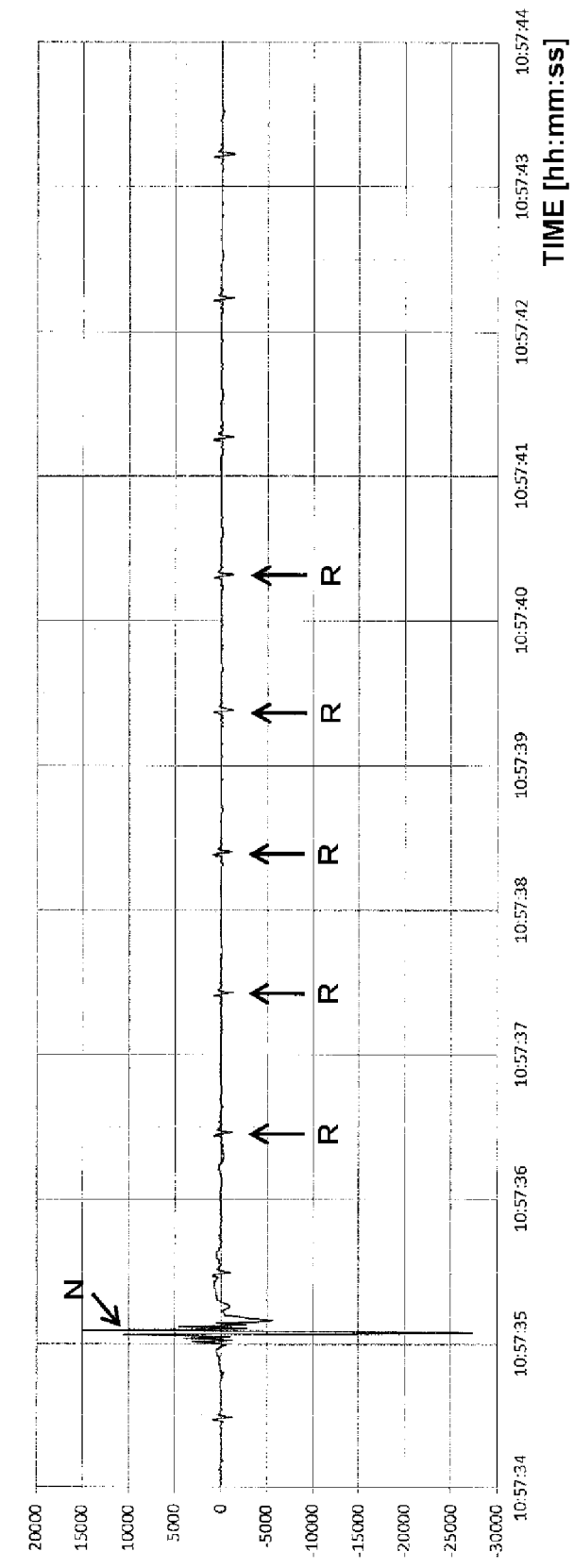
FIG. 4 is a timing chart showing the time difference value of the electrocardiographic waveform shown in FIG. 3.

FIG. 4 is a timing chart showing a time difference value y of the ECG waveform shown in FIG. 3, in which the abscissa represents time and the ordinate represents a difference value [μV] of the cardiac potential. In FIGS. 3 and 4, a sampling period is 5 ms. By obtaining the time difference of the ECG waveform, a downward peak along with a sudden decrease in cardiac potential from an R wave to an S wave appears at each position of "R" in FIG. 4 along with the rhythm of heartbeats. Furthermore, at the position of "N", a peak derived from noise appears.

The index value calculation unit 4 calculates an index value for heartbeat detection based on the time difference value y calculated by the time difference value calculation unit 3 (step S3 of FIG. 2). More specifically, the index value calculation unit 4 calculates, for each sampling time, as the index value, a value obtained by inverting the positive or negative sign of a subtraction result. This subtraction result is obtained by subtracting the smallest value among the time difference values from the time difference value y at time T in which the calculation is targeted; the time difference values being the time difference value y in a predetermined time domain of (T−Δt2) to (T−Δt1) that is before time T in which the calculation is targeted and the time difference value y in a predetermined time domain of (T+Δt1) to (T+Δt2) that is after time T in which the calculation is targeted.

That is, when yT represents the time difference value at time T of the calculation target, and ymin represents the smallest value of the time difference value in the predetermined time domain before time T in which the calculation is targeted and that in the predetermined time domain after time T in which the calculation is targeted, an index value I at time T in which the calculation is targeted is given by:

$$I=-(yT-y\min) \quad (2)$$

In this embodiment, Δt2>Δt1 is satisfied, and Δt1=25 ms and Δt2=150 ms are set. Note that the positive or negative sign of the subtraction result is inverted in order to set a peak derived from the R wave to a positive value.

Figure 5:
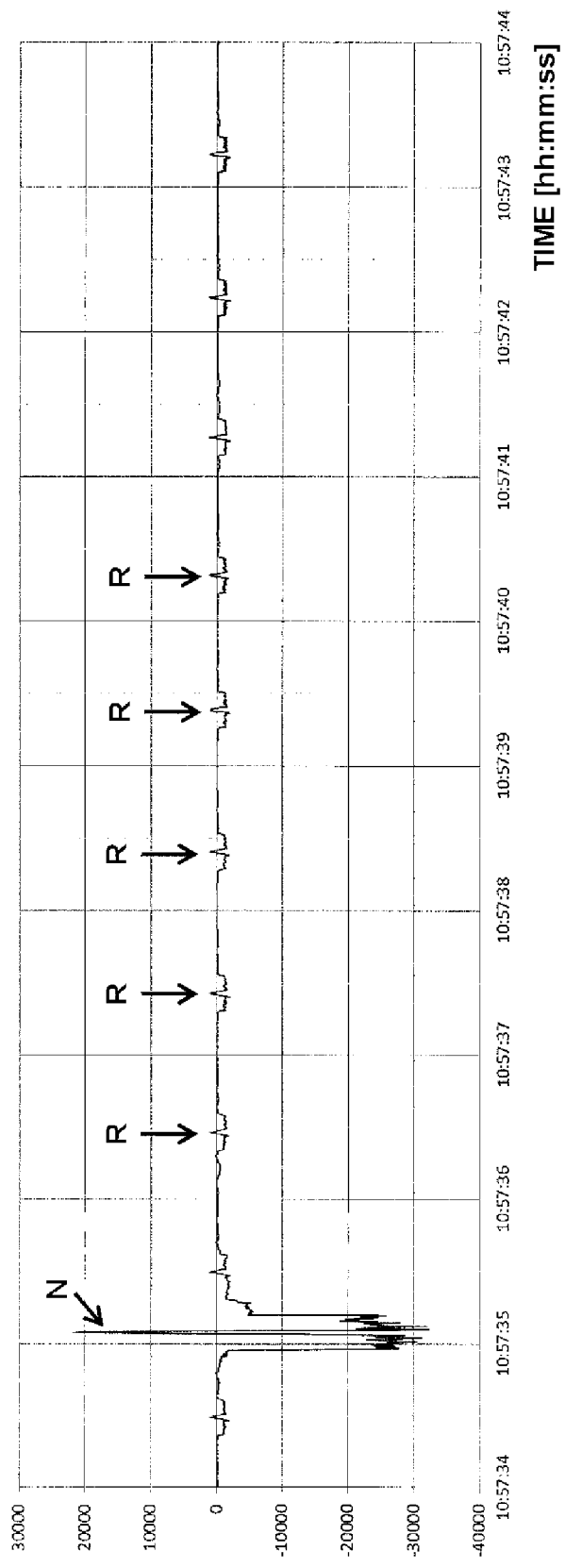
FIG. 5 is a timing chart showing an index value calculated from the time difference value of the electrocardiographic waveform shown in FIG. 4.

FIG. 5 is a timing chart showing the index value I calculated from the time difference value of the ECG waveform shown in FIG. 4. As in FIGS. 3 and 4, the unit of the ordinate is a potential [μV]. The index I represents, for a peak derived from the R wave, the height of the clearance of the time difference value in the time domain in the periphery of the peak, thereby enhancing the peak derived from the R wave. Therefore, it is possible to detect the R wave by applying, to a data string of the index value I, a peak search using a threshold. However, a peak derived from noise indicated by "N" is enhanced equally, and its value is about 20,000 μV. Consequently, when the threshold setting unit 5 sets a threshold, it is needed to be aware of the peak derived from the noise.

Figure 6:
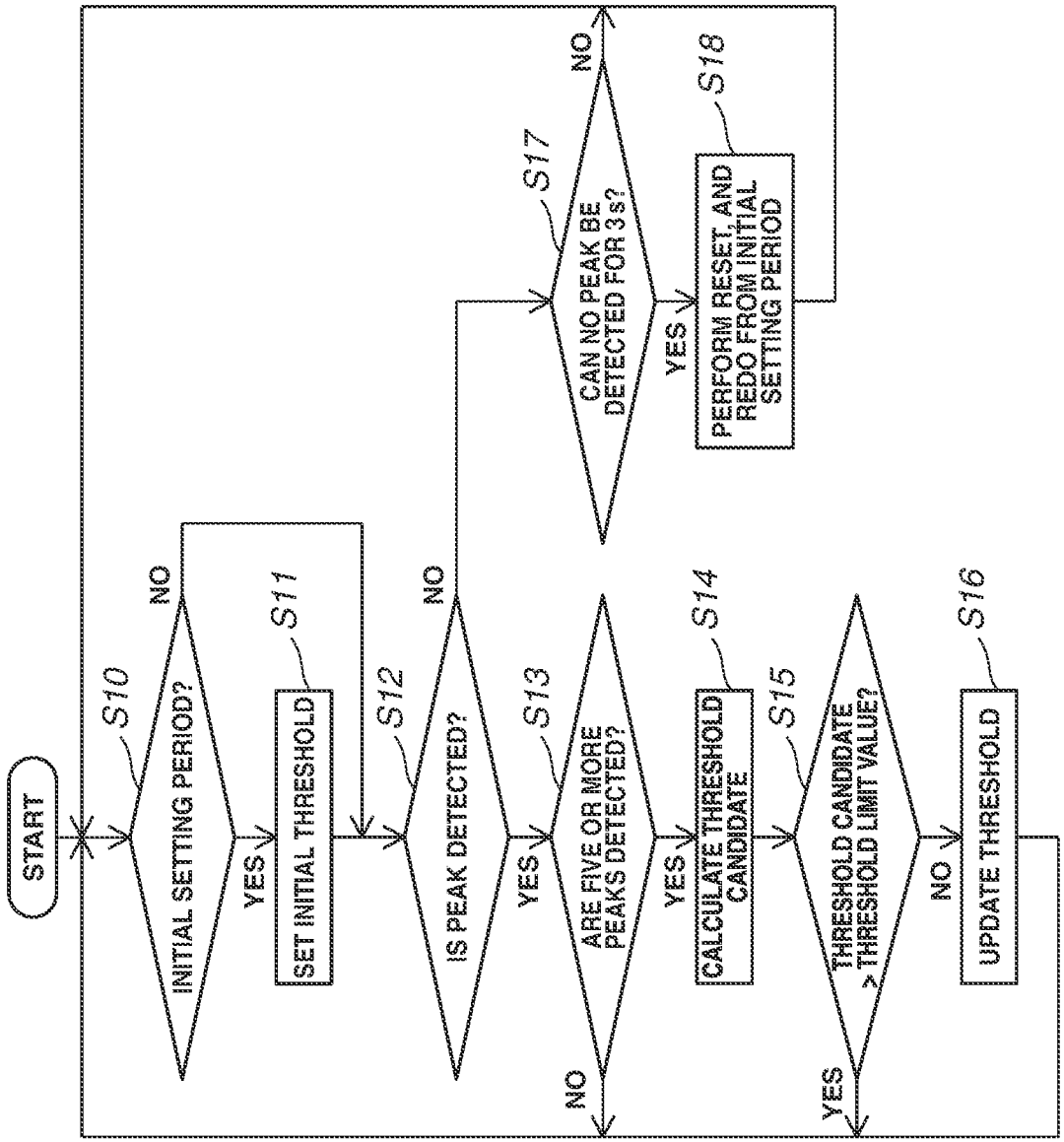
FIG. 6 is a flowchart for explaining details of the operation of a threshold setting unit of the heartbeat detection device according to the first embodiment of the present invention.

FIG. 6 is a flowchart for explaining details of the operation (step S4 of FIG. 2) of the threshold setting unit 5. During the initial setting period of the threshold (YES in step S10 of FIG. 6), the threshold setting unit 5 obtains a maximum value Imax using data of the index value I in the initial setting period, and sets, as an initial threshold Th, a value obtained by multiplying the maximum value Imax by a predetermined coefficient α (for example, α=0.4) (step S11 of FIG. 6), given by:

$$Th=\alpha \times I\max \quad (3)$$

Note that the initial setting period indicates a period of 2 s from the start of measurement of a heartbeat or a period of 2 s from when a peak search operation is reset, as will be described later.

The threshold setting unit 5 determines whether the peak of the index value I exceeding the current threshold Th can be detected (step S12 of FIG. 6). When a predetermined number V (in this embodiment, V=5) or more of peaks can be detected consecutively (YES in step S13 of FIG. 6), an average value Iave of the predetermined number V of the most recent peaks among these consecutively detected peaks is obtained, and multiplied by a predetermined coefficient β (for example, β=0.4), and the thus obtained value is set as a threshold candidate Thc (step S14 of FIG. 6), given by:

$$Thc=\beta \times Iave \quad (4)$$

The threshold setting unit 5 compares the calculated threshold candidate Thc with a threshold limit value L based on the current threshold Th and a difference limit value that appears more likely be the time difference value of the ECG wave of a human. When the threshold candidate Thc exceeds the threshold limit value L, the threshold Th is not updated (YES in step S15 of FIG. 6); otherwise (NO in step S15), the candidate Thc is set as the new threshold Th (step S16 of FIG. 6). The threshold limit value L will be described later.

The threshold setting unit 5 performs the above processing for each sampling time. When the peak of the index value I exceeding the threshold Th is detected consecutively, the threshold candidate Thc is successively calculated by repeatedly executing the processing in step S14. When the threshold candidate Thc is equal to or smaller than the threshold limit value L, the threshold Th is updated.

When the peak of the index value I exceeding the threshold Th cannot be detected for 3 seconds after initially setting the threshold Th or after updating the threshold Th (YES in step S17 of FIG. 6), the threshold setting unit 5 resets the peak search operation, and returns to the initial setting period to again carry out setting of the threshold Th (step S18 of FIG. 6).

Next, when the peak of the index value I exceeding the threshold Th is detected (YES in step S5 of FIG. 2), the heartbeat time determination unit 6 sets the sampling time of the peak as a heartbeat time (step S6 of FIG. 2). The sampling time information can be acquired from the storage unit 2.

By repeating the processes in steps S1 to S6 for each sampling time, time-series data containing multiple heartbeat time points are obtained.

Figure 7:
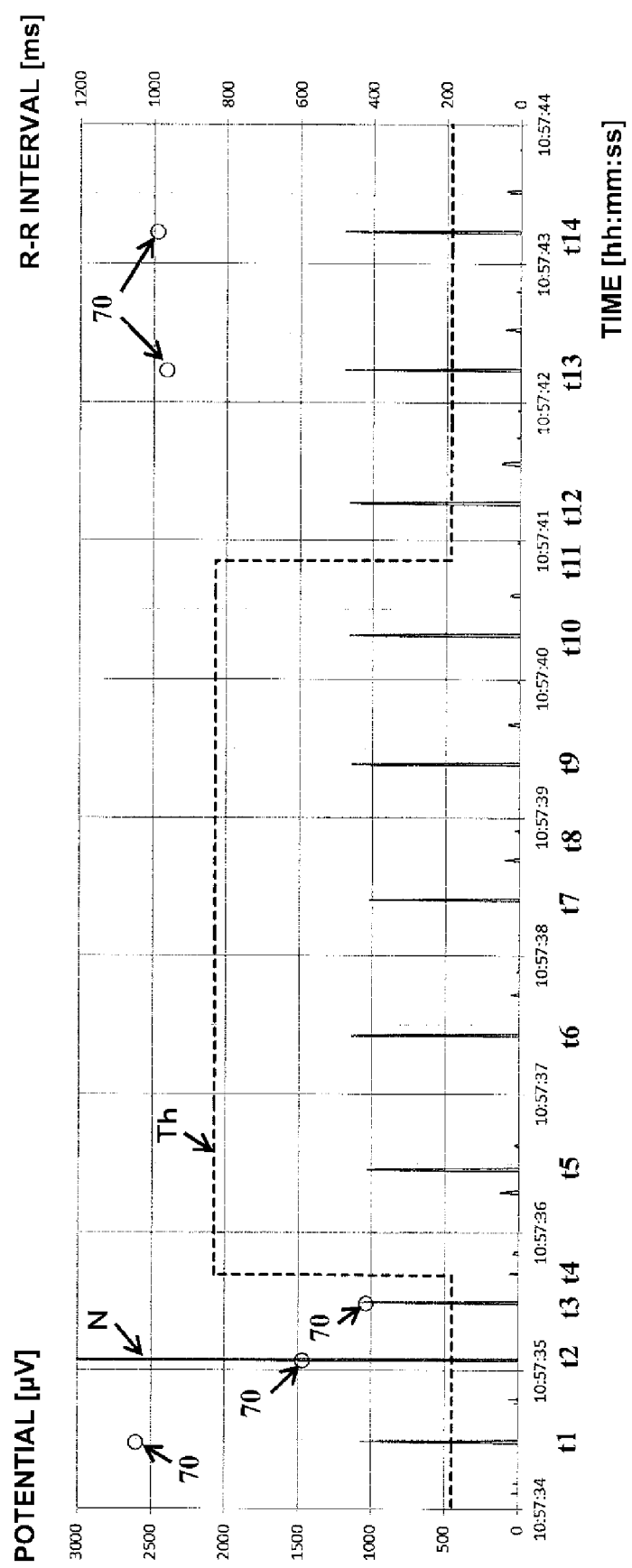
FIG. 7 is an enlarged timing chart of FIG. 5.

FIG. 7 is a timing chart displayed by magnifying a range from 0 to 3,000 µV of the ordinate in FIG. 5. A broken line represents the threshold Th set at each time. The threshold Th indicates a value when the threshold candidate Thc is taken directly and set as the new threshold Th without performing the processes in steps S15 and S16 among the processes of the threshold setting unit 5 described with reference to FIG. 6. Each ○ mark 70 indicates an R-R interval [ms] calculated from the heartbeat time that has been determined by the heartbeat time determination unit 6 based on the threshold Th shown in FIG. 7. Note that the graph of FIG. 7 is displayed by extracting a portion of a continuous data string. R wave detection is executed from a point of time before time shown in the graph.

In the example shown in FIG. 7, after the peak of the index value I derived from the R wave exceeds the threshold Th at time t1, the peak of the index value I derived from noise exceeds the threshold Th at time t2, and the peak is recognized as a heartbeat. Thus, the value of the R-R interval is output. However, the value of the R-R interval (the interval between time points t1 and t2) is about 600 ms, and is smaller than the original value. After that, the peak of the index value I derived from the R wave exceeds the threshold Th at time t3. However, since the peak at time t2 is detected as a heartbeat, the value of the R-R interval (the interval between time points t2 and t3) is also small.

In addition, the threshold Th is updated at time t4 by the processing of the threshold setting unit 5. However, since the value of the peak of the index value I derived from noise is incorporated, the threshold Th jumps from 448 µV to 2,075 µV. Since the threshold Th jumps, peaks derived from R waves at subsequent time points t5, t6, t7, t9, and t10 are smaller than the threshold Th, and are not unwantedly detected as heartbeats.

Since the peak of the index value I exceeding the threshold Th cannot be detected for 3 seconds after updating the threshold Th, the threshold setting unit 5 resets the peak search operation at time t8, and a period of 2 seconds after that is used for setting of the initial threshold. The new threshold Th is set at time t11, and the peak of the index value I derived from the R wave exceeds the threshold Th at time t12, and is detected as a heartbeat. Subsequently, the peak of the index value I derived from the R wave is detected as a heartbeat at time t13, and the value of the R-R interval is output. At time t13, the value of the R-R interval returns to a normal value close to 1,000 ms. That is, in the example shown in FIG. 7, a situation in which heartbeat detection does not function for 5 seconds or longer occurs due to mixing of a large noise.

Consider a possible maximum value of the time difference of the ECG waveform of a human, and conversely, a value that is unlikely be the time difference of the ECG waveform of a human. A QRS interval (from the beginning of a Q wave to the end of an S wave) is 0.06 to 0.1 seconds (see Yamasawa, "Easy-to-Understand Electrocardiogram, Reveal Heart Disease from 12-lead Electrocardiogram", Elsevier Japan, 2003).

A time that takes from the highest value of the R wave to the lowest value of the S wave can be considered to be about 15 to 25 ms as ¼ of the QRS interval. Furthermore, during the time from the highest value of the R wave to the lowest value of the S wave, the value changes near the center most suddenly. Assuming that the time range of the change is about half the time from the highest value of the R wave to the lowest value of the S wave, the time range can be estimated to be about 7.5 to 12.5 ms. Assuming that during this time range, a change in cardiac potential corresponding to a QRS amplitude occurs, it is considered that the rate of change in the cardiac potential is about 350 µV/ms at the most. When the rate of change of the cardiac potential is converted to a time difference value obtained by equation (1), 700 µV is obtained for a sampling interval of 1 ms, and is largely rounded to 1,000 µV by giving a margin.

As described above, when the sampling interval is 1 ms, a time difference value exceeding 1,000 µV is unlikely be the time difference of the ECG waveform of a human. The standard value is set to 5,000 µV for a sampling interval of 5 ms. That is, when dT represents the sampling interval, a difference limit value X that is likely be the time difference value of the ECG waveform of a human is given by:

$$X = dT \text{ [ms]} \times 1000 \text{ [µV]} \tag{5}$$

As described above, the index value I shown in FIG. 5 indicates, for the peak derived from the R wave, the height of the clearance of the time difference value in the time domain in the periphery of the peak. When the time difference value of the ECG waveform includes a large noise, and the noise presents a sharp single peak, in the worst case, the value directly affects the index value I.

When a value obtained by multiplying, by the coefficient β=0.4, the average value Iave of the predetermined number V (in this embodiment, V=5) of peaks exceeding the current threshold Th is set as a new threshold Th', when p represents the standard peak value of the index value I, the updated threshold Th' is normally about Th'=p×β=p×0.4. When an abnormal noise with a peak value X is generated for once, the next threshold Th' increases by (X−p)/5×0.4=0.08X−0.2Th. When X=5000 µV, 400−0.2Th [µV] is obtained. That is, when the sampling interval is 5 ms, when the increase amount of the next threshold Th' with respect to the current threshold Th exceeds 400−0.2Th [µV], there is a greater probability that the threshold is being influenced by the noise.

In this embodiment, when the threshold candidate Thc calculated in step S14 exceeds the threshold limit value L=400+0.8Th [µV] (=Th+400−0.2Th) with respect to the current threshold Th (YES in step S15), the threshold Th is not updated. Note that the general formula of the threshold limit value L is given by:

$$L = Th + (\beta/V)x - (1/V)Th \tag{6}$$

Figure 8:
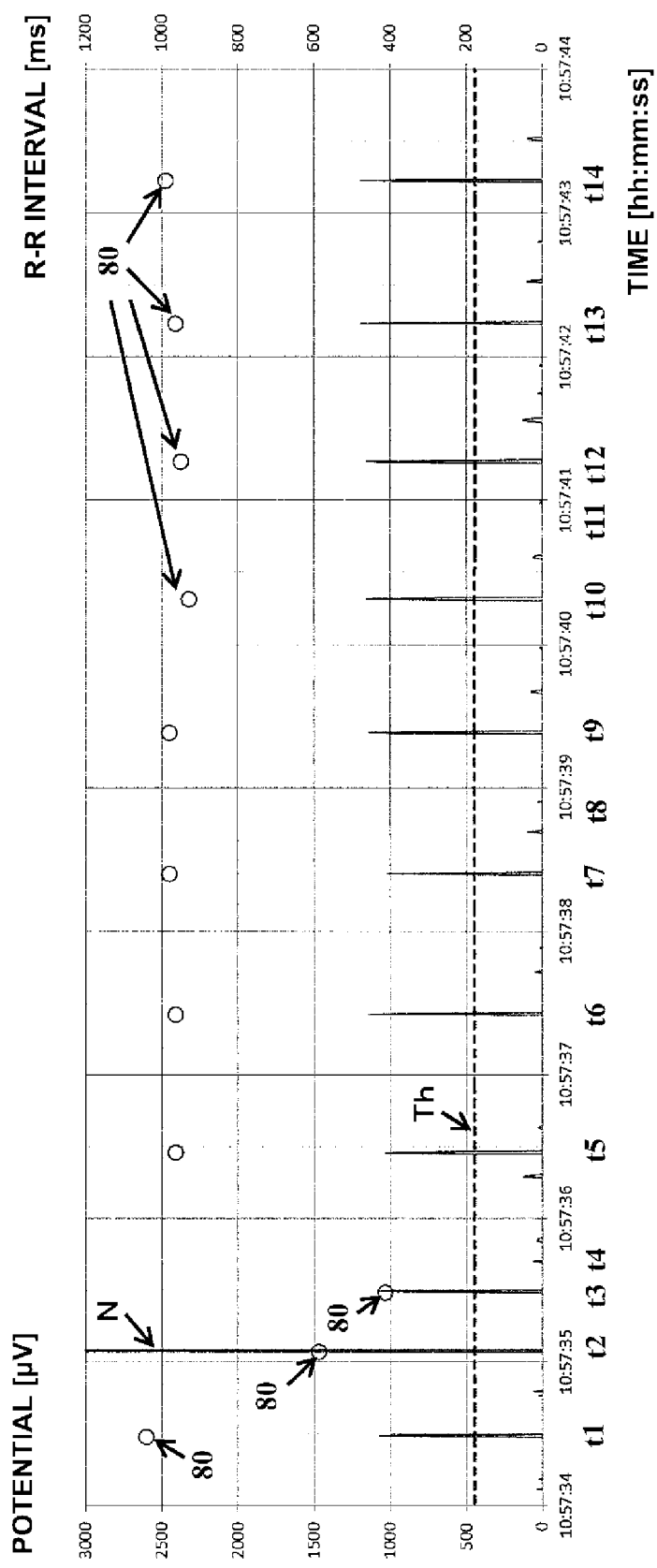
FIG. 8 is a timing chart showing a result of the heartbeat detection method according to the first embodiment of the present invention.

FIG. 8 is a timing chart displayed by magnifying a range from 0 to 3,000 µV of the ordinate in FIG. 5. Unlike FIG. 7, FIG. 8 shows a result obtained when the processes in steps S15 and S16 described with reference to FIG. 6 are performed. Each ○ mark 80 indicates an R-R interval [ms] calculated from the heartbeat time that has been determined by the heartbeat time determination unit 6 based on the threshold Th shown in FIG. 8.

The threshold Th at time t1 is 448 µV. After the peak of the index value I derived from the R wave exceeds the threshold Th at time t1, and the peak of the index value I derived from noise exceeds the threshold Th at time t2. Thus, the threshold candidate Thc=2075 µV is calculated based on the value of the peak. At this time, the threshold limit value L=400+0.8Th=758.4 µV is obtained. Since the threshold candidate Thc=2075 µV exceeds the threshold limit value L, the threshold Th is not updated by the processing in step S15, and the threshold Th=448 μV will be continuously used. As a result, according to this embodiment, unlike FIG. 7, it is apparent that peaks derived from R waves at time points t5, t6, t7, t9, and t10 are detected appropriately.

As described above, according to this embodiment, it is possible to detect a heartbeat more appropriately even if a noise is superimposed on the ECG waveform.

Second Embodiment

Figure 9:
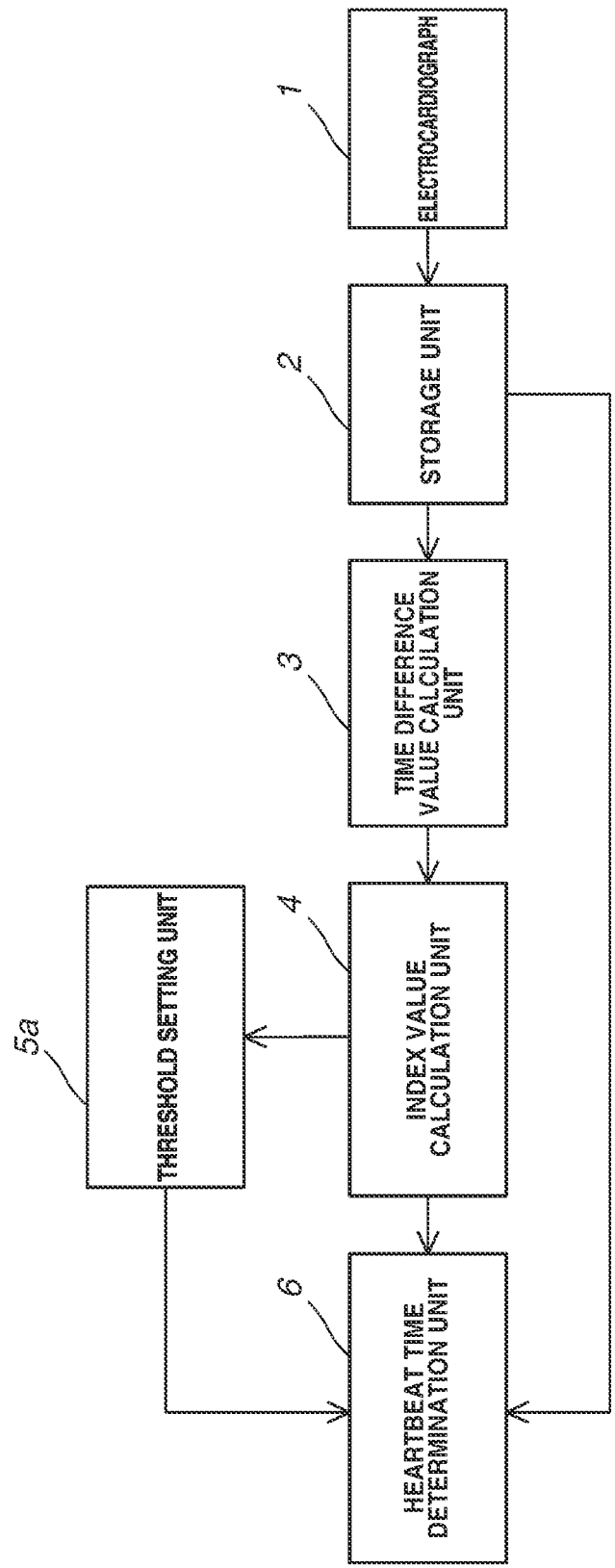
FIG. 9 is a block diagram showing the arrangement of a heartbeat detection device according to the second embodiment of the present invention.

The second embodiment of the present invention will be described. FIG. 9 is a block diagram showing the arrangement of a heartbeat detection device according to the second embodiment of the present invention. The same reference numerals as in FIG. 1 denote the same components. The heartbeat detection device according to this embodiment includes an electrocardiograph 1, a storage unit 2, a time difference value calculation unit 3, an index value calculation unit 4, a threshold setting unit 5a, and a heartbeat time determination unit 6.

In this embodiment, the difference from the first embodiment is the operation of the threshold setting unit 5a. The operation of the threshold setting unit 5a will be described with reference to FIG. 6. Processes in steps S10 to S15, S17, and S18 of FIG. 6 are the same as those of the threshold setting unit 5 according to the first embodiment.

When updating a threshold Th in step S16, the threshold setting unit 5a according to this embodiment uses a value obtained by averaging a current threshold Th (i−1) and a threshold candidate Thc(i) calculated in step S14. That is, when Th(i) represents the updated threshold, the threshold setting unit 5a calculates the threshold Th(i) by:

$$Th(i)=r\times Thc(i)+(1-r)\times Th(i-1) \qquad (7)$$

In equation (7), r represents a predetermined coefficient (for example, r=0.1). In this way, when updating the threshold Th, it is possible to suppress a sudden shift of the threshold Th by averaging the current threshold Th and the threshold candidate Thc, thereby achieving stability. The remaining components are as described in the first embodiment.

Figure 10:
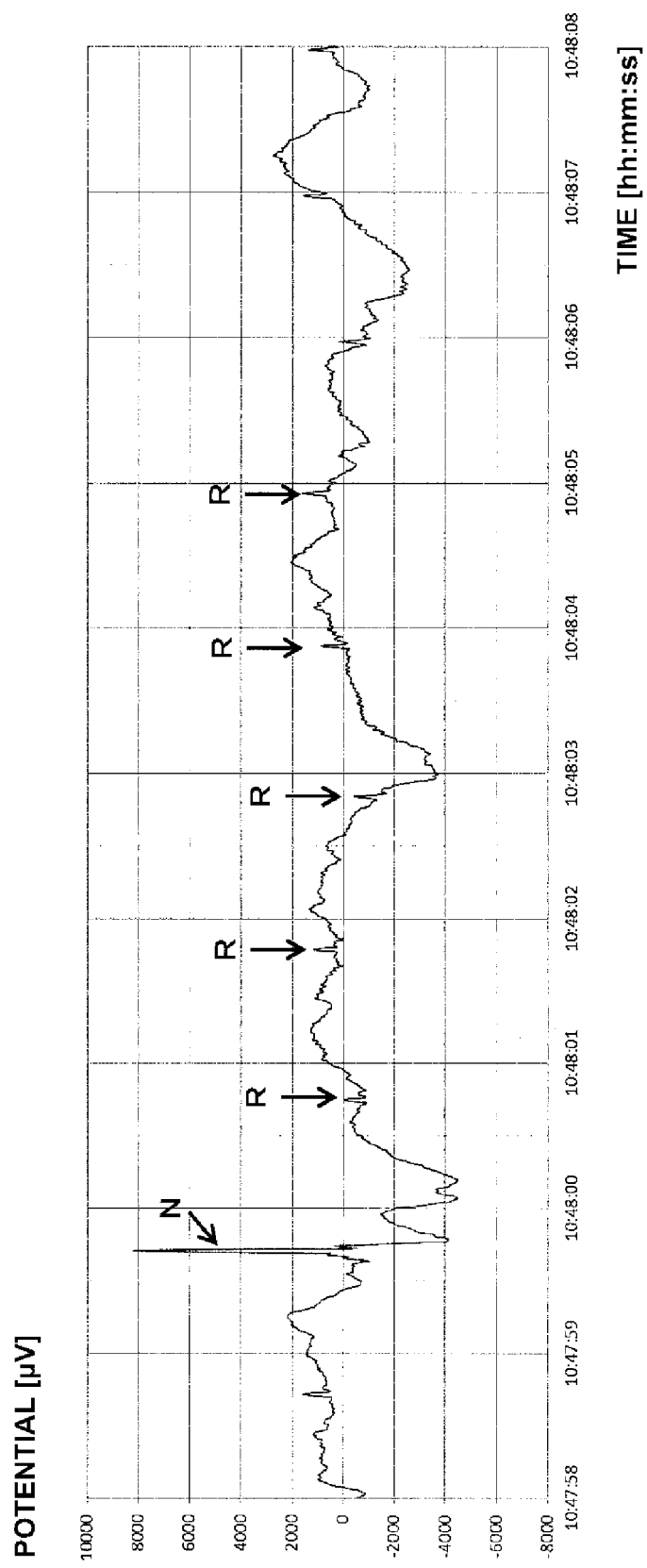
FIG. 10 is a timing chart showing another example of an electrocardiographic waveform.

FIG. 10 is a timing chart showing another example of an ECG waveform. As in FIG. 3, "R" in FIG. 10 represents an R wave to be detected as a heartbeat. In the example shown in FIG. 10, the baseline of the ECG waveform undulates and, in addition to this, the waveform is largely disturbed at a position of "N". The potential at the position of "N" reaches 8,000 μV. It is apparent that the disturbance of the waveform is caused not by the cardiac potential but by the noise.

Figure 11:
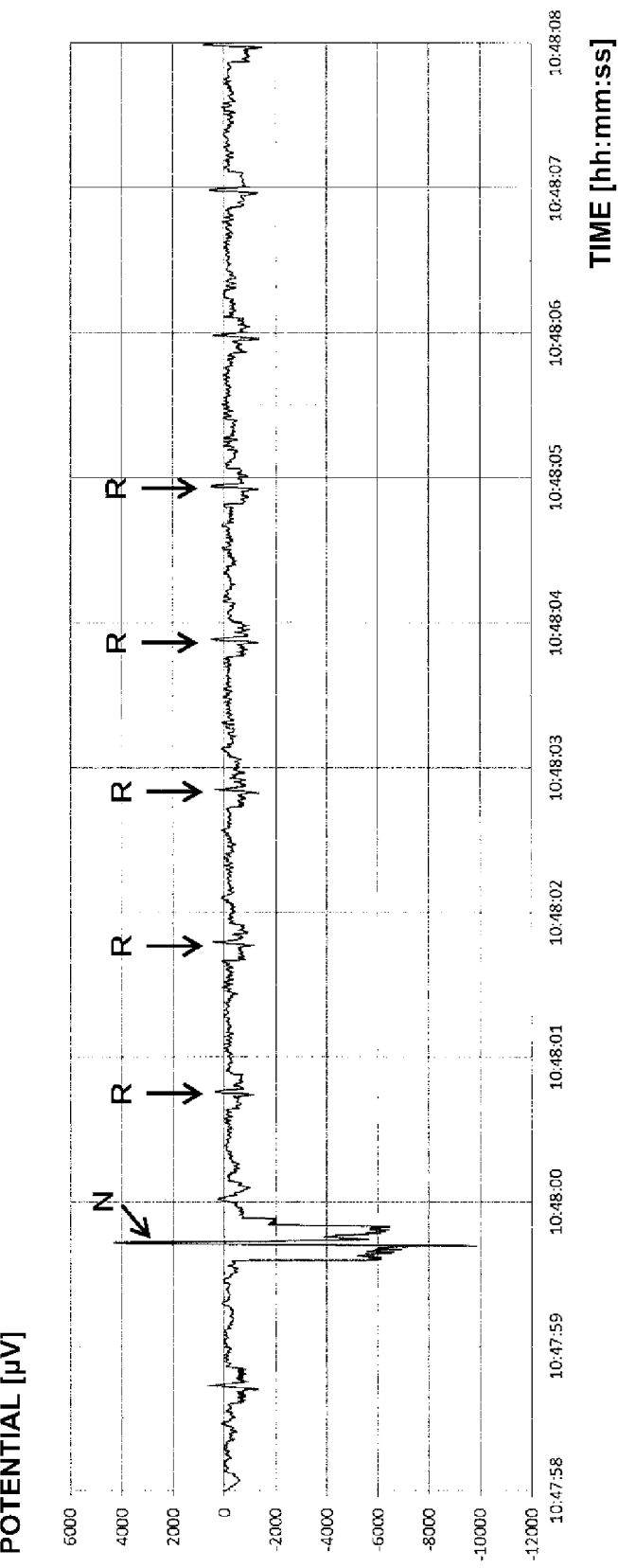
FIG. 11 is a timing chart showing an index value calculated from the electrocardiographic waveform shown in FIG. 10.

FIG. 11 is a timing chart showing an index value I calculated from the ECG waveform shown in FIG. 10 in the same manner as in the first embodiment. As shown in FIG. 5, a peak derived from a noise indicated by "N", is being enhanced, and thus the value of the peak reaches about 4,000 μV.

Figure 12:
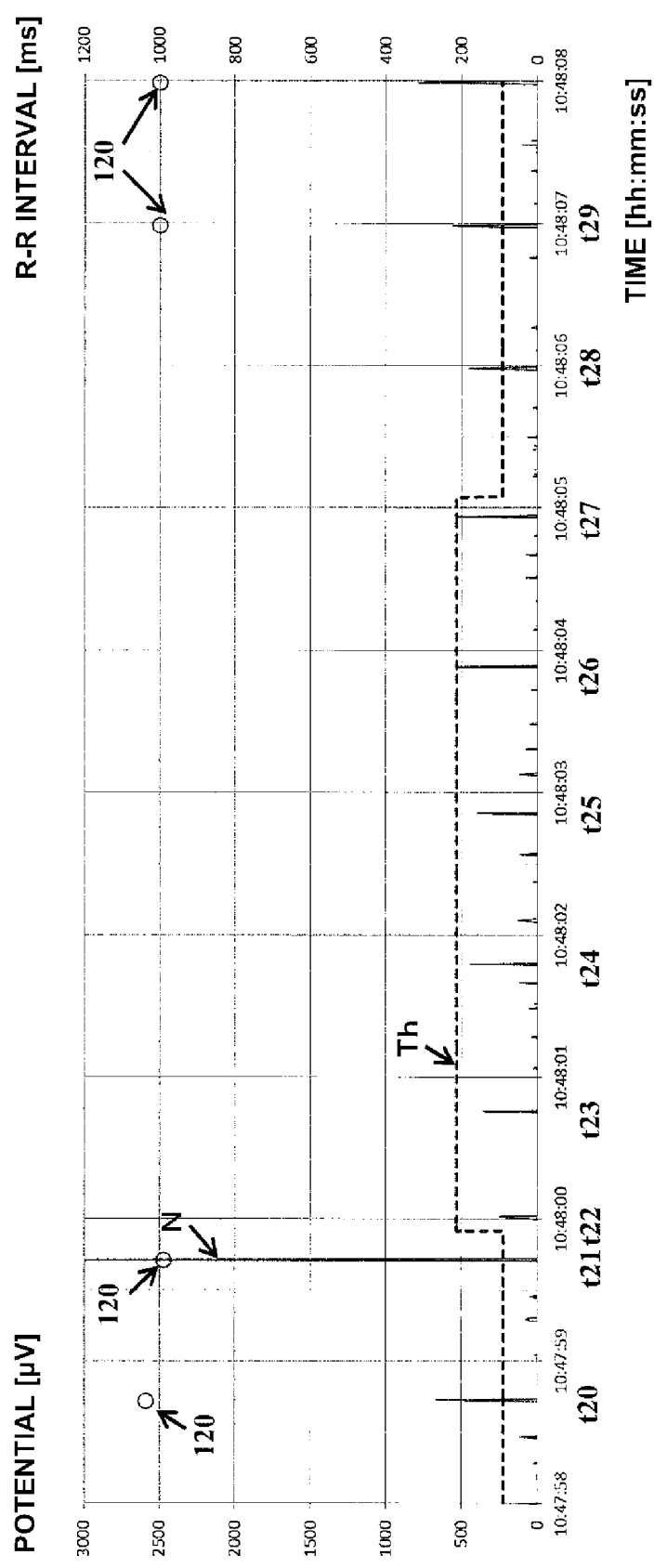
FIG. 12 is an enlarged timing chart of FIG. 11.

FIG. 12 is a timing chart displayed by magnifying a range from 0 to 3,000 μV of the ordinate in FIG. 11. A broken line represents the threshold Th set at each time. This threshold Th indicates a value obtained when the threshold setting unit 5 according to the first embodiment is used, instead of the threshold setting unit 5a described in this embodiment. Each ○ mark 120 indicates an R-R interval [ms] calculated from a heartbeat time that has been determined by the heartbeat time determination unit 6 based on the threshold Th shown in FIG. 11. Note that the graph in FIG. 11 is displayed by extracting a portion of a continuous data string. R wave detection is executed from a point of time before time shown in the graph.

In the example shown in FIG. 12, after the peak of the index value I derived from the noise exceeds the threshold Th at time t21, the threshold Th is updated at time t22. Since, however, a threshold candidate Thc=531 μV is equal to or smaller than a threshold limit value L=400+0.8Th=578 μV, the threshold candidate Thc is adopted as the threshold Th without any modification to the value of threshold candidate, and the value of threshold Th is increased from 222 μV to 531 μV. The reason why the threshold candidate Thc does not exceed the threshold limit value L is that the value of the peak derived from the noise is slightly lower than that in the case shown in FIGS. 3 and 5. Since the threshold Th increases, peaks derived from R waves at subsequent time points t23, t24, t25, t26, and t27 are smaller than the threshold Th, and are not detected as heartbeats unwantedly.

Figure 13:
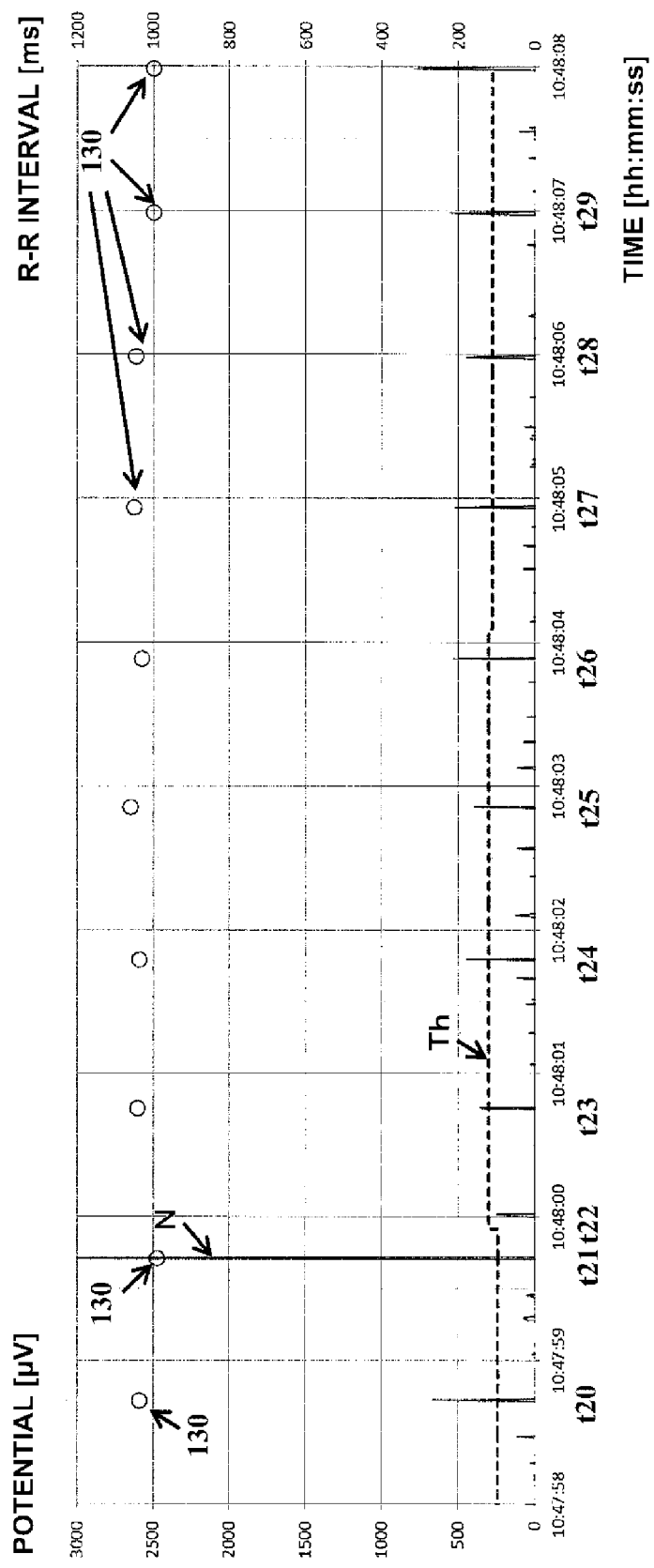
FIG. 13 a timing chart showing a result of a heartbeat detection method according to the second embodiment of the present invention.

FIG. 13 is a timing chart displayed by magnifying a range from 0 to 3,000 μV of the ordinate in FIG. 11. Unlike FIG. 12, FIG. 13 shows a result obtained when the threshold setting unit 5a according to this embodiment is used. Each ○ mark 130 indicates an R-R interval [ms] calculated from the heartbeat time that has been determined by the heartbeat time determination unit 6 based on the threshold Th shown in FIG. 13.

The threshold Th at time t20 is 222 μV, as described above. After the peak of the index value I derived from the noise exceeds the threshold Th at time t21, when the threshold Th is updated at time t22, the threshold candidate Thc=531 μV is equal to or smaller than the threshold limit value L=578 μV. Since, however, the threshold setting unit 5a sets, as the new threshold Th, a value obtained by averaging the threshold Th=222 μV and the threshold candidate Thc=531 μV, the updated threshold Th is about 250 μV, thereby suppressing any increase in the threshold Th. As a result, according to this embodiment, unlike the case shown in FIG. 12, peaks derived from R waves at time points t23, t24, t25, t26, and t27 are detected appropriately.

As described above, according to this embodiment, it is possible to eliminate the influence of noise that cannot be eliminated in the first embodiment, thereby detecting a heartbeat more appropriately.

Third Embodiment

Figure 14:
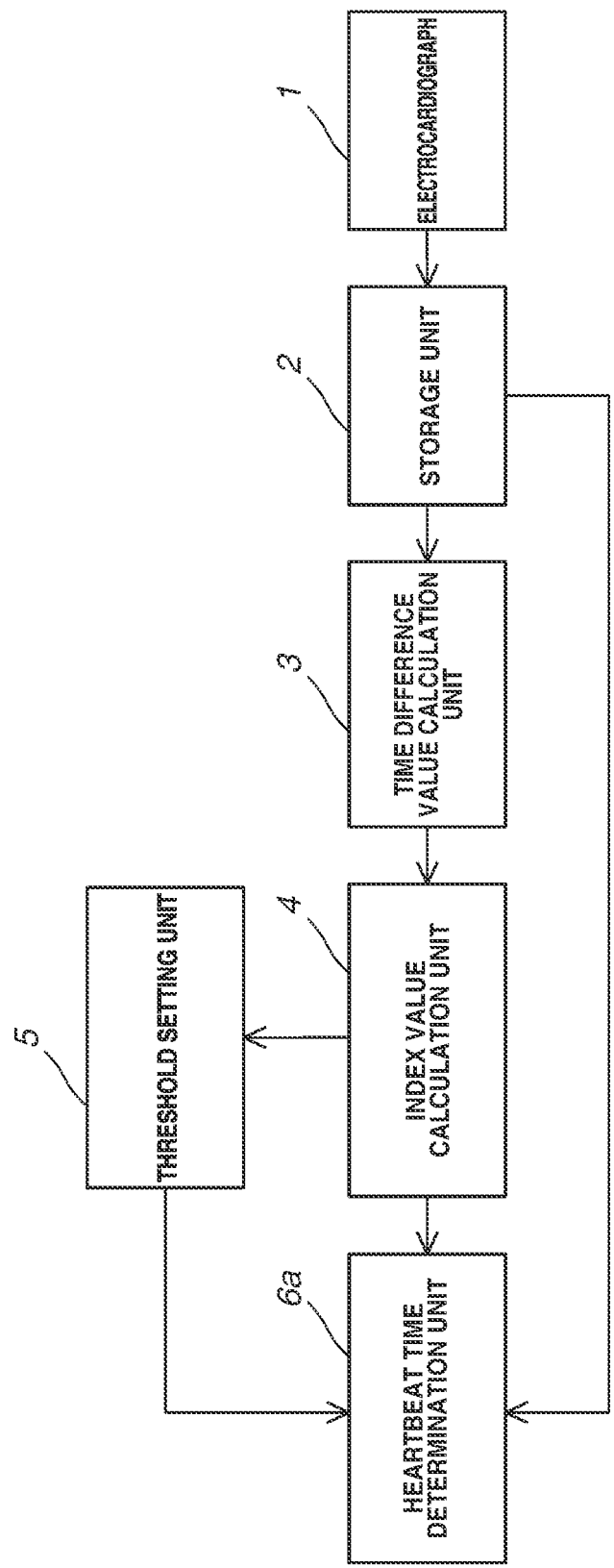
FIG. 14 is a block diagram showing the arrangement of a heartbeat detection device according to the third embodiment of the present invention.

The third embodiment of the present invention will be described next. FIG. 14 is a block diagram showing the arrangement of a heartbeat detection device according to the third embodiment of the present invention. The same reference numerals as in FIG. 1 denote the same components. The heartbeat detection device according to this embodiment includes an electrocardiograph 1, a storage unit 2, a time difference value calculation unit 3, an index value calculation unit 4, a threshold setting unit 5, and a heartbeat time determination unit 6a.

Figure 15:
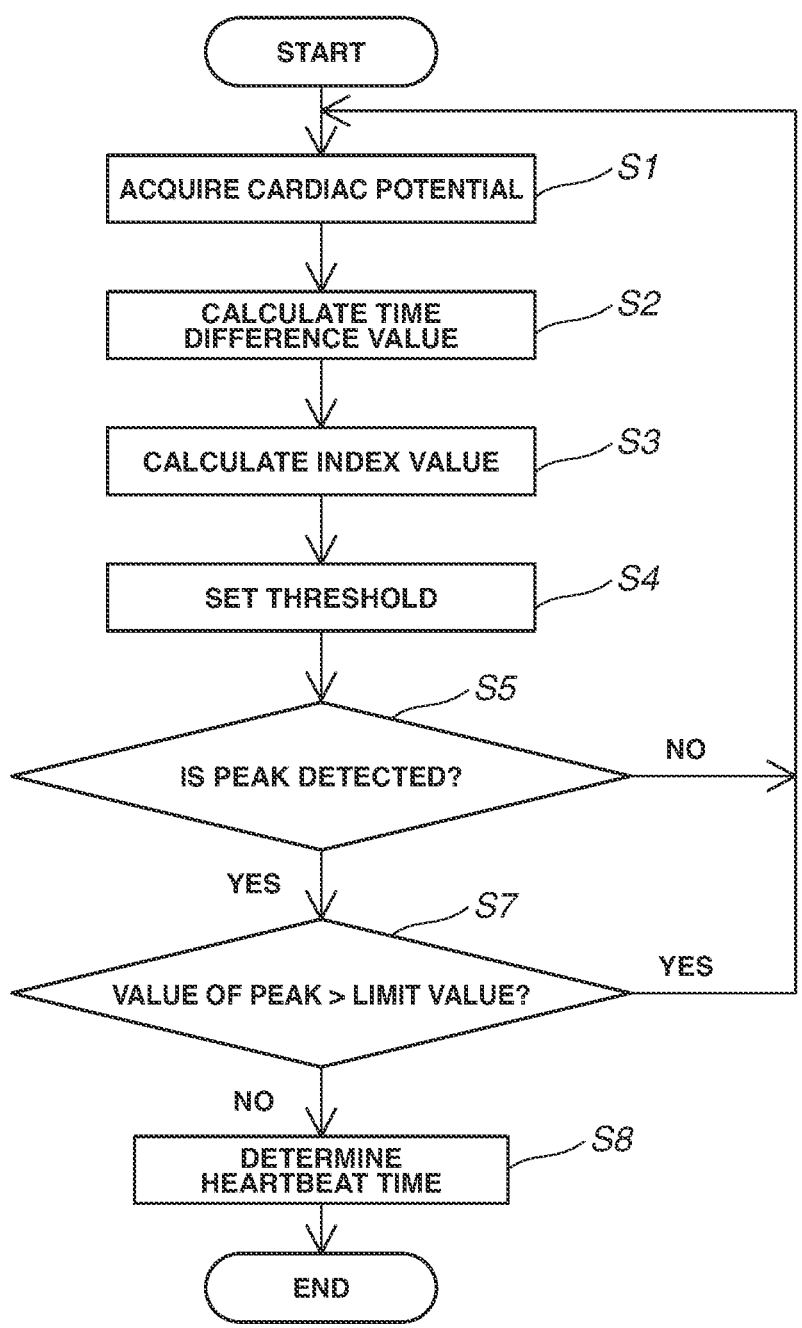
FIG. 15 is a flowchart for explaining a heartbeat detection method according to the third embodiment of the present invention.

In this embodiment, the difference from the first embodiment is the operation of the heartbeat time determination unit 6a, and thus the operation of the heartbeat time determination unit 6a will be described. FIG. 15 is a flowchart for explaining a heartbeat detection method according to this embodiment.

When the peak of an index value I exceeding a threshold Th is detected (YES in step S5 of FIG. 15), the heartbeat time determination unit 6a according to this embodiment compares the value of the peak with an index limit value Z that is likely be the index value I. When the value of the peak exceeds the index limit value Z (YES in step S7 of FIG. 15), the peak is not detected as a heartbeat; otherwise (NO in step S7), the sampling time of the peak is set as a heartbeat time (step S8 of FIG. 15). The limit value Z that can be said to be likely an index value derived from an ECG waveform of a human is, for example, 5,000 µV (for a sampling interval of 5 ms).

Figure 16:
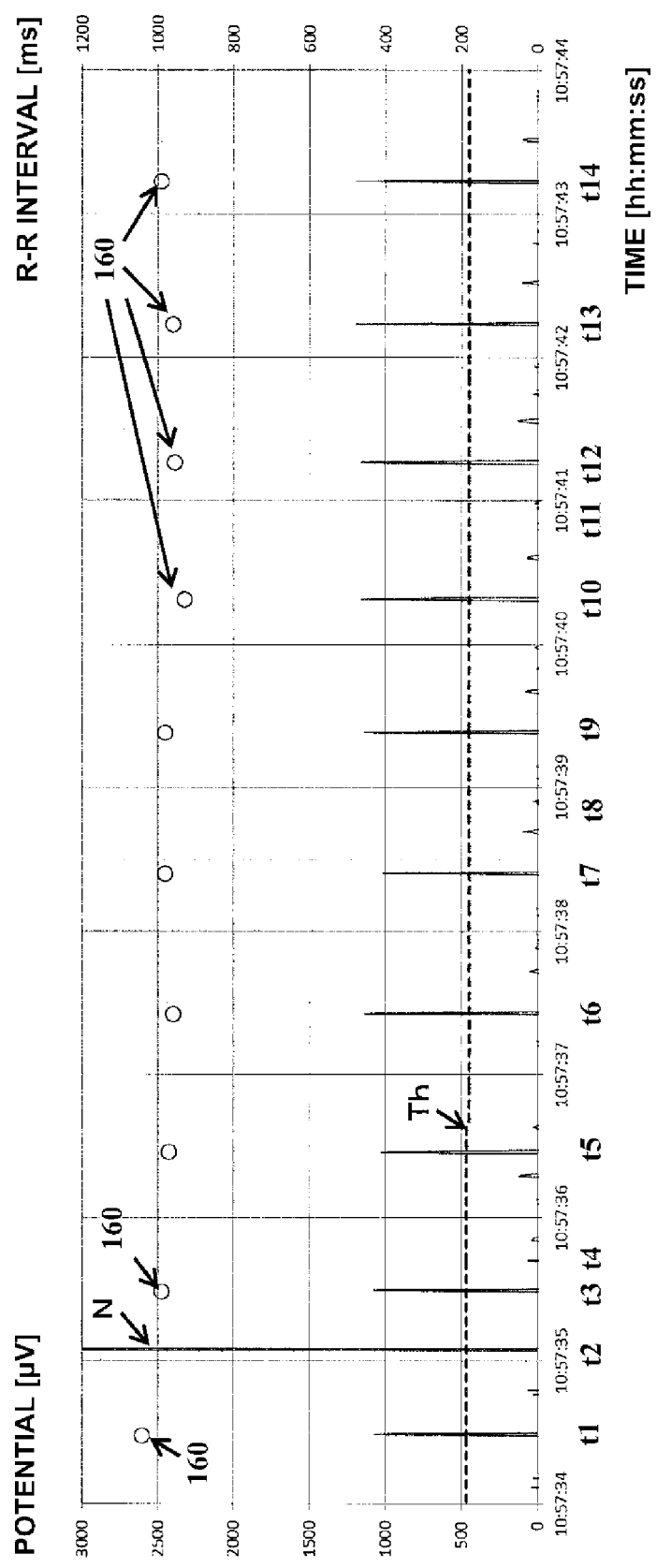
FIG. 16 is a timing chart showing a result of the heartbeat detection method according to the third embodiment of the present invention.

FIG. 16 is a timing chart showing a result according to this embodiment, and displayed by magnifying a range from 0 to 3,000 µV of the ordinate in FIG. 5 and superimposing the threshold Th, as in FIG. 8. Each ○ mark 160 indicates an R-R interval [ms] calculated from the heartbeat time that has been determined by the heartbeat time determination unit 6a based on the threshold Th shown in FIG. 16.

In the example shown in FIG. 8 according to the first embodiment, since the peak of the index value I derived from the noise exceeds the threshold Th at time T2, and is recognized as a heartbeat, the value of the R-R interval is output. However, the value of the R-R interval (the interval between time points t1 and t2) is about 600 ms, and is smaller than the original value.

To the contrary, in this embodiment, the threshold Th is the same as in the first embodiment. Since, however, the value of the peak of the index value I exceeds the index limit value Z at time t2, the heartbeat time determination unit 6a does not detect the peak as a heartbeat. As a result, the R-R interval (the interval between times t1 and t3) calculated from a heartbeat detected at time t3 is set to a correct value close to 1,000 ms.

In this way, in this embodiment, it is possible to detect a heartbeat more appropriately than in the first embodiment.

Note that this embodiment has explained the case in which the heartbeat time determination unit 6a is applied to the first embodiment. The same may apply to the second embodiment, as a matter of course.

Figure 17:
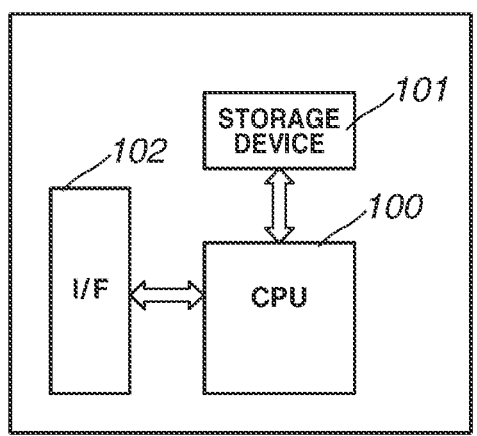
FIG. 17 is a block diagram showing an example of the arrangement of a computer for implementing the heartbeat detection device according to each of the first to third embodiments of the present invention.

The storage unit 2, time difference value calculation unit 3, index value calculation unit 4, threshold setting unit 5 or 5a, and heartbeat time determination unit 6 or 6a described in each of the first to third embodiments can be implemented by a computer including a CPU (Central Processing Unit), a storage device, and an interface, and a program for controlling these hardware resources. FIG. 17 shows an example of the arrangement of this computer. The computer includes a CPU 100, a storage device 101, and an interface device (to be referred to as an I/F hereinafter) 102. The I/F 102 is connected to the electrocardiograph 1 and the like. In this computer, a program for implementing the heartbeat detection method of the present invention is provided while being recorded on a recording medium such as a flexible disk, CD-ROM, DVD-ROM, or memory card, and stored in the storage device 101. The CPU 100 executes the processing described in each of the first to third embodiments in accordance with the program stored in the storage device 101.

INDUSTRIAL APPLICABILITY

The present invention is applicable to a technique of detecting heartbeats of a living body.

EXPLANATION OF THE REFERENCE NUMERALS AND SIGNS

1 . . . electrocardiograph, 2 . . . storage unit, 3 . . . time difference value calculation unit, 4 . . . index value calculation unit, 5, 5a . . . threshold setting unit, 6, 6a . . . heartbeat time determination unit

The invention claimed is:

1. A heartbeat detection device configured to detect a heartbeat time from a sampling data string obtained by sampling an electrocardiographic waveform of a living body at sampling times with a time interval therebetween, the heartbeat detection device comprising:
a time difference value calculation unit configured to calculate, for each of the sampling times, a time difference value between two consecutive sampling data involved in the sampling data string;
an index value calculation unit configured to calculate, for each of the sampling times, an index value for a heartbeat detection based on the time difference values calculated by the time difference value calculation unit;
a threshold setting unit configured to determine whether a peak of the index values that exceeds a current threshold is detected, configured to calculate, when consecutively detecting equal to or greater than a predetermined number of peaks, a threshold candidate based on an average value of most recent predetermined number of peaks among the peaks of equal to or greater than the predetermined number that are being detected, configured not to update the current threshold when the threshold candidate exceeds a threshold limit value, and configured to set the threshold candidate as a new threshold when the threshold candidate does not exceed the threshold limit value; and
a heartbeat time determination unit configured to set, when the peak of the index values exceeding a current threshold is detected, the sampling time of the peak as the heartbeat time,
wherein the index value calculation unit is configured to obtain a smallest value ymin among the time difference values in a time domain including a first predetermined time domain before a sampling time T for which the index value is to be calculated and a second predetermined time domain after the sampling time T, subtract the smallest value ymin from the time difference value yT calculated by the time difference value calculation unit for the sampling time T, invert the positive or negative sign of a subtraction result (yT−ymin), and set the inverted subtraction result −(yT−ymin) as the index value for the sampling time T.

2. The heartbeat detection device according to claim 1, wherein the heartbeat time determination unit compares, when detecting the peak of the index values exceeding a current threshold, a value of the peak with an index limit value, and does not set the sampling time of the peak as the heartbeat time when the value of the peak exceeds the index limit value, and sets the sampling time of the peak as the heartbeat time when the value of the peak does not exceed the index limit value.

3. The heartbeat detection device according to claim 1, wherein the threshold setting unit is further configured to set, as an initial threshold, a value based on a maximum value of the index values in an initial setting period; and, when the peak of the index value exceeding the threshold is not detected for a predetermined time after initially setting the threshold or updating the threshold, return to the initial setting period to again carry out setting of the threshold.

4. A heartbeat detection device configured to detect a heartbeat time from a sampling data string obtained by sampling an electrocardiographic waveform of a living body at sampling times with a time interval therebetween, the heartbeat detection device comprising:
a time difference value calculation unit configured to calculate, for each of the sampling times, a time difference value between two consecutive sampling data involved in the sampling data string;

an index value calculation unit configured to calculate, for each of the sampling times, an index value for a heartbeat detection based on the time difference values calculated by the time difference value calculation unit;

a threshold setting unit configured to determine whether a peak of the index values that exceeds a current threshold is detected, configured to calculate, when consecutively detecting equal to or greater than a predetermined number of peaks, a threshold candidate based on an average value of most recent predetermined number of peaks among the peaks of equal to or greater than the predetermined number that are being detected, and configured not to update the current threshold when the threshold candidate exceeds a threshold limit value, and configured to set a value obtained by averaging the current threshold and the threshold candidate as a new threshold when the threshold candidate does not exceed the threshold limit value; and a heartbeat time determination unit configured to set, when the peak of the index values exceeding a current threshold is detected, the sampling time of the peak as the heartbeat time, wherein the index value calculation unit is configured to obtain a smallest value ymin among the time difference values in a time domain including a first predetermined time domain before a sampling time T for which the index value is to be calculated and a second predetermined time domain after the sampling time T, subtract the smallest value ymin from the time difference value yT calculated by the time difference value calculation unit for the sampling time T, invert the positive or negative sign of a subtraction result (yT−ymin), and set the inverted subtraction result −(yT−ymin) as the index value for the sampling time T.

5. The heartbeat detection device according to claim 4, wherein the heartbeat time determination unit compares, when detecting the peak of the index values exceeding a current threshold, a value of the peak with an index limit value, and does not set the sampling time of the peak as the heartbeat time when the value of the peak exceeds the index limit value, and sets the sampling time of the peak as the heartbeat time when the value of the peak does not exceed the index limit value.

6. The heartbeat detection device according to claim 4, wherein the threshold setting unit is further configured to set, as an initial threshold, a value based on a maximum value of the index values in an initial setting period; and, when the peak of the index value exceeding the threshold is not detected for a predetermined time after initially setting the threshold or updating the threshold, return to the initial setting period to again carry out setting of the threshold.

* * * * *